(12) United States Patent
Kennedy et al.

(10) Patent No.: US 8,209,130 B1
(45) Date of Patent: Jun. 26, 2012

(54) SEQUENCE ASSEMBLY

(75) Inventors: Caleb Kennedy, Arlington, MA (US); Gregory J. Porreca, Cambridge, MA (US)

(73) Assignee: Good Start Genetics, Inc., Cambridge, MA (US)

( * ) Notice: Subject to any disclaimer, the term of this patent is extended or adjusted under 35 U.S.C. 154(b) by 0 days.

(21) Appl. No.: 13/439,508

(22) Filed: Apr. 4, 2012

(51) Int. Cl.
*G06F 19/00* (2011.01)
*C12Q 1/68* (2006.01)

(52) U.S. Cl. ........................................ 702/20; 435/6.11

(58) Field of Classification Search .................. None
See application file for complete search history.

(56) References Cited

OTHER PUBLICATIONS

Klein et al. LOCAS-A low coverage assembly tool for resequencing projects. PLoS ONE vol. 6, article 23455 (2011).*

* cited by examiner

*Primary Examiner* — John S Brusca
(74) *Attorney, Agent, or Firm* — Thomas C. Meyers (57) ABSTRACT

The invention relates to assembly of sequence reads. The invention provides a method for identifying a mutation in a nucleic acid involving sequencing nucleic acid to generate a plurality of sequence reads. Reads are assembled to form a contig, which is aligned to a reference. Individual reads are aligned to the contig. Mutations are identified based on the alignments to the reference and to the contig.

12 Claims, 3 Drawing Sheets

SEQUENCE ASSEMBLY

FIELD OF THE INVENTION

The invention relates to assembly of sequence reads.

BACKGROUND

Methods to sequence or identify significant fractions of the human genome and genetic variations within those segments are becoming commonplace. However, a major impediment to understanding health implications of variations found in every human being remains unraveling of the functional meaning of sequence differences in individuals. Sequencing is an important first step that allows geneticists and physicians to develop a full functional understanding of that data.

Next-generation sequencing (NGS) technologies include instruments capable of sequencing more than $10^{14}$ kilobasepairs (kbp) of DNA per instrument run. Sequencing typically produces a large number of independent reads, each representing anywhere between 10 to 1000 bases of the nucleic acid. Nucleic acids are generally sequenced redundantly for confidence, with replicates per unit area being referred to as the coverage (i.e., "10× coverage" or "100× coverage"). Thus, a multi-gene genetic screening can produce millions of reads.

When a genetic screening is done for a person, the resulting reads can be compared to a reference, such as a published human genome. This comparison generally involves either assembling the reads into a contig and aligning the contig to the reference or aligning each individual read to the reference.

Assembling reads into a contig and aligning the contig to a reference produces unsatisfactory results due to the algorithms used for contig assembly. Generally, algorithms for contig assembly assess a read using certain quality criteria. Those criteria set a threshold at which certain reads that satisfy the algorithm are determined to be legitimate reads that are used to assemble the contigs, while reads that do not satisfy the algorithm are excluded from the contig assembly process. Based on the threshold level of the algorithm, as many as 10% of legitimate sequence reads are excluded from further analysis.

Additionally, aligning the resulting contig to a reference is error prone due to a tradeoff, inherent in doing an alignment, between whether mismatches or gaps (insertions/deletions, or "indels") are favored. When one sequence is aligned to another, if one sequence does not match the other perfectly, either gaps must be introduced into the sequences until all the bases match or mismatched bases must appear in the alignment. Existing approaches to alignment involve algorithms with good mismatch sensitivity at the expense of indel sensitivity or good indel sensitivity at the expense of mismatch sensitivity. For example, if an alignment is to detect mismatches with sufficient fidelity, then it is likely that some indels will be missed.

Even where assembly provides accurate detection of variants (e.g., substitutions or indels), these methods are often computationally intractable for high throughput data analysis because each read must be compared to every other read in a dataset to determine sequence overlap and build contigs.

Another sequence assembly technique involves aligning each individual read to a reference. This assembly technique is problematic because very short reads (e.g., 50 bp or less) may align well in a number of places on a very long reference (e.g., 5 million bp). With a number of equally good positions to align to, aligning a read to a reference offers little positional accuracy. Also, particularly with very short reads, long indels can be difficult or impossible to detect. Due in part to the tradeoff between substitution sensitivity and indel sensitivity, certain mutation patterns are particularly difficult to detect. Indels near the ends of reads are sometimes incorrectly interpreted as short strings of mismatched bases. Substitutions near indels are often interpreted incorrectly, as well.

Existing methods of read assembly do not offer the positional accuracy of a contig-based alignment while including detailed information from each read. Further, due to limitations in alignment algorithms, existing methods do a poor job of correctly interpreting certain mutations (e.g., indels near the ends of reads, substitutions near indels).

SUMMARY

The invention generally relates to genotyping nucleic acids through methods of assembling and aligning sequence reads. Methods of the invention combine a contig based sequence assembly approach with an individual alignment based sequence assembly approach in order to more accurately assemble sequence reads. Methods of the invention are accomplished by assembling contigs from sequence reads, aligning the contigs to a reference sequence, aligning the reads back to the contig, and identifying mutations via the assembled contig and the alignments. By assembling reads into contigs as well as aligning the individual reads to the contigs, the need to compare each of the reads to all of the others is avoided, providing computational tractability even for very high throughput analyses. Information about variants in the sample is identified through the alignment of the contigs to the reference. After aligning each raw read, the alignment of the read to the contig is used to map positional information and any identified differences (i.e., variant information) from the reference to the raw read. The raw read is then translated to include positional and variant information, allowing genotyping to be performed using the aligned translated reads.

By these methods, positional accuracy of reads is obtained and the limitations of a tradeoff between substitution sensitivity and deletion sensitivity are overcome. By combining data in this way, an accurate and sensitive interpretation of the nucleic acid is obtained and an accurate description of a genotype including an identity and a location of a mutation on an organism's genome is reported.

Generally, nucleic acid obtained from a subject is sequenced to produce a plurality of reads. Sequencing the nucleic acid may be by any method known in the art. For example, sequencing may involve pyrosequencing, sequencing-by-synthesis, reversible dye-terminators, or sequencing by hybridization.

The reads produced by sequencing are assembled into one or more contigs. Assembly into contigs may be by any method including: collection into subsets based on, for example, barcodes, primers, or probe sets; a heuristic method; or any traditional assembly algorithm known in the art. For example, assembly de novo can include an assembly using a greedy algorithm. A computer processor can select the two reads from a plurality that exhibit the most overlap, join them to produce a new read, and repeat, thereby assembling the reads produce an contig. In certain embodiments, assembly includes positioning the reads relative to each other by making reference to a reference genome. This occurs where, for example, the subject nucleic acid is sequenced as captured by molecular inversion probes, because the start of each read derives from a genomic position that is known and specified by the probe set design.

Where a number of different probe sets are used, the full set of raw reads can be organized into subsets according to an associated probe. The number of reads that must be cross-compared is reduced substantially, providing computational tractability for very high throughput data sets. In some embodiments, extrinsic knowledge of probe position (i.e., relative offset in reference genome) is used to aid in positioning the reads. By collecting each read per probe and/or positioning each read according to a known relative offset, reads can be assigned to contigs a priori, further improving specificity of positional information.

In some embodiments, the reads may contain barcode information. Barcode, generally, refers to any sequence information used for identification, grouping, or processing. For example, barcode information may be inserted into template nucleic acid during sample prep or sequencing. Barcodes can be included to identify individual reads, groups of reads, subsets of reads associated with probes, subsets of reads associated with exons, subsets of reads associated with samples or any other group, or any combination thereof. For example, by sequencing sample and barcode information, reads can be sorted (e.g., using a computer processor) by sample, exon, probe set, etc., or combination thereof, through reference to the barcode information. The reads may be assembled into contigs by reference to the barcode information. A computer processor can identify the barcodes and assemble the reads by positioning the barcodes together.

Reads are assembled into contigs. In the case of a single, homozygous target nucleic acid, a single contig per location is typically produced. In other cases such as, for example, multiple patient multiplexed analyses, heterozygous targets, a rare somatic mutation, or a mixed sample, two or more contigs can be produced. Each contig can be represented as a consensus sequence, i.e., a probable interpretation of the sequence of the nucleic acid represented by that contig.

Each contig is aligned to a reference genome. Where, for example, two contigs were found for a given exon, both align to the same reference position, but one may contain variant information that the other does not. In certain embodiments, positioning a contig along a reference genome involves indexing the reference, for example, with a Burrows-Wheeler Transform (BWT). Indexing a reference can be done by computer programs known in the art, for example, Burrows-Wheeler Aligner (BWA) available from the SourceForge web site maintained by Geeknet (Fairfax, Va.) using the bwa-sw algorithm. Contigs may then be aligned to the indexed reference. For example, where the bwa-sw algorithm is implemented by BWA, parameters of the alignment are optimized to ensure correct placement of the contig on the overall reference genome. In some embodiments, protein-coding sequence data in a contig, consensus sequence, or reference genome, is represented by amino acid sequence and a contig is aligned to a reference genome with reference to the amino acid sequence.

With each contig aligned to the reference genome, any differences between the contig and the reference genome can be identified. Since the entire contig with contiguous sequence from many overlapping reads is positioned against the reference genome, the added sequence context increases the likelihood that the correct position is identified whereby variant information (e.g., mismatches and gaps) can be transferred transiently and with high fidelity from reference to contig and from contig to reads. Thus, any indels introduced here likely represent differences between the nucleic acid and the reference. Each mutation identified here can be described with reference to the reference genome. In certain embodiments, a computer program creates a file or variable containing a description of the mutation (e.g., a compact idiosyncratic gapped alignment report (CIGAR) string).

With the contigs aligned, each raw read is aligned to a contig in a local, contig-specific alignment. In certain embodiments, a pairwise alignment is performed between the read and the contig. In some embodiments, all reads align as a perfect match to at least one contig. For example, BWA with bwa-short can be used to align each read to a contig, and the output can be a Binary Alignment Map (BAM) including, for example, a CIGAR string. A file or variable can record the results of the local, contig-specific alignment (e.g., as a CIGAR string).

Each raw read-to-contig alignment is mapped to the reference using the corresponding contig-to-reference alignment. By using the contig as a vehicle, positional and variant information relative to the reference is provided for each read, allowing each raw read alignment to be translated to include positional and variant information relative to the reference genome.

Genotyping is performed using the translated, aligned reads. Raw quality scores (e.g., for substitutions) can be included. The output of the local alignment, describing the read compared to the contig, can be combined with the output of the reference alignment, describing the contig compared to the reference. This combination gives, for any mutation detected in the nucleic acid, a description of that mutation relative to the reference genome. Wild type and mutant alleles including specific mutations can be identified. Mutation patterns previously thought to pose particular difficulty (e.g., long indels, indel-proximal substitutions, and indels near the ends of reads) are identified with fidelity. Methods of the invention can perform, with high-throughput data using existing computer power, sequencing and genotyping analyses that were previously computationally intractable.

By combining information in this way, the limitations of a tradeoff between substitution sensitivity and deletion sensitivity is overcome. The output includes an accurate and sensitive interpretation of the subject nucleic. This provides an accurate description of a genotype including an identity and a location of a mutation on an organism's genome.

The output can be provided in the format of a computer file. In certain embodiments, the output is a VCF file, FASTA file, XML file, or similar containing sequence data such as a sequence of the nucleic acid aligned to a sequence of the reference genome. In certain embodiments, the output contains coordinates or a string describing one or more mutations in the subject nucleic acid relative to the reference genome. In some embodiments, the output is a sequence alignment map (SAM) or binary alignment map (BAM) file comprising a CIGAR string.

The output describes a mutation in the nucleic acid. Mutations detectable by methods of the invention include substitutions, single nucleotide polymorphisms, insertions, deletions, translocations, epigenetic mutations, and copy number repeats. Methods of the invention detect and describe more than one mutation including, for example, two or more mutations. Mutations can be detected that are near each other, for example less than about 1,000 nucleotides apart along a strand of nucleic acid. In a preferred embodiment, methods of the invention can detect two mutations within about 100 bases of each other, such as, for example, within about 10 bases or about 5 bases of each other. Methods of the invention can detect two mutations of different types near each other including, for example, a substitution near an indel. Mutations near the ends of sequence reads can be detected including, for example, an indel at or near an end of a read.

In certain embodiments, a sample is heterogeneous (e.g., includes heterogeneous tumor, circulating fetal, or other DNA) and at least some of the individual reads include variations relative to the contig. Mutations in individual reads can be detected when each raw read is aligned to a contig in a local, contig-specific alignment. Parameters of this alignment can be optimized to ensure very highly sensitive detection of mutations and combinations of mutations. For example, because the position relative to the reference genome is established with confidence, a gap penalty can be decreased relative to a substation probability. By these methods, the individual reads can be examined to detect any mutations including, for example, mutations specific to that read or only a few reads. That is, a difference between the reference and an individual read is determined using differences between the read and the contig plus differences between the contig and the reference. For example, a contig may map to the reference with a 1 bp substitution, and a read may map to the contig with a 8 bp deletion. Methods of the invention give the correct annotation for the read, relative to the reference, as a description including a 8 bp deletion as well as a 1 bp substitution.

DETAILED DESCRIPTION

The invention generally relates to a method for identifying a mutation in a nucleic acid. The invention provides methods for genetic screening of one or multiple genes or other nucleic acid sequences. Genetic screening can include screening for a mutation, which can be a disease-associated mutation, where the nucleic acid comes from a sample obtained from a patient. Methods of the invention can also be used in a test for heterozygosity, or loss thereof, in a tumor.

Nucleic acid in a sample can be any nucleic acid including, for example, genomic DNA in a tissue sample, cDNA amplified from a particular target in a laboratory sample, or mixed DNA from multiple organisms. In some embodiments, the sample includes homozygous DNA from a haploid or diploid organism. For example, a sample can include genomic DNA from a patient who is homozygous for a rare recessive allele. In other embodiments, the sample includes heterozygous genetic material from a diploid organism such that two alleles are present in substantially equal amounts. In certain embodiments, the sample includes genetic material from a diploid or polyploid organism with a somatic mutation such that two related nucleic acids are present in allele frequencies other than 50 or 100%, i.e., 20%, 5%, 1%, 0.1%, or any other allele frequency.

In one embodiment, nucleic acid template molecules (e.g., DNA or RNA) are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. Biological samples for use in the present invention include viral particles or preparations. Nucleic acid template molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin, e.g. amplified/isolated DNA from the freezer.

Generally, nucleic acid can be extracted from a biological sample by a variety of techniques such as those described by Maniatis, et al., Molecular Cloning: A Laboratory Manual, 1982, Cold Spring Harbor, N.Y., pp. 280-281; Sambrook and Russell, Molecular Cloning: A Laboratory Manual 3Ed, Cold Spring Harbor Laboratory Press, 2001, Cold Spring Harbor, N.Y.; or as described in U.S. Pub. 2002/0190663.

Nucleic acid obtained from biological samples may be fragmented to produce suitable fragments for analysis. Template nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydroshear instrument. Generally, individual nucleic acid template molecules can be from about 2 kb bases to about 40 kb. In a particular embodiment, nucleic acids are about 6 kb-10 kb fragments. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In one embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-$C_6H_4$—($OCH_2$—$CH_2$)$_x$OH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C 14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethyl-ammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

In various embodiments, the nucleic acid is amplified, for example, from the sample or after isolation from the sample. Amplification refers to production of additional copies of a nucleic acid sequence and is generally carried out using polymerase chain reaction or other technologies well known in the art (e.g., Dieffenbach and Dveksler, PCR Primer, a Laboratory Manual, 1995, Cold Spring Harbor Press, Plainview, N.Y.). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany, F., Genome Research, 1:5-16 (1991); Barany, F., PNAS, 88:189-193 (1991); U.S. Pat. No. 5,869,252; and U.S. Pat. No. 6,100,099), strand displacement amplification and restriction fragments length polymorphism, transcription based amplification system, rolling circle amplification, and hyperbranched rolling circle amplification. Further examples of amplification techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), RT-PCR-RFLP, hot start PCR, in situ polonony PCR, in situ rolling circle amplification (RCA), bridge PCR, picotiter PCR and emulsion PCR. Other suitable amplification methods include transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and length of the primer pairs yield the desired melting temperature. The simplest equation for determining the melting temperature of primers smaller than 25 base pairs is the Wallace Rule (Td=2 (A+T)+4(G+C)). Computer programs can also be used to design primers, including but not limited to Array Designer Software from Arrayit Corporation (Sunnyvale, Calif.), Oligonucleotide Probe Sequence Design Software for Genetic Analysis from Olympus Optical Co., Ltd. (Tokyo, Japan), NetPrimer, and DNAsis Max v3.0 from Hitachi Solutions America, Ltd. (South San Francisco, Calif.). The TM (melting or annealing temperature) of each primer is calculated using software programs such as OligoAnalyzer 3.1, available on the web site of Integrated DNA Technologies, Inc. (Coralville, Iowa).

With PCR, it is possible to amplify a single copy of a specific target sequence in genomic DNA to a level that can be detected by several different methodologies (e.g., staining; hybridization with a labeled probe; incorporation of biotinylated primers followed by avidin-enzyme conjugate detection; or incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

Amplification adapters may be attached to the fragmented nucleic acid. Adapters may be commercially obtained, such as from Integrated DNA Technologies (Coralville, Iowa). In certain embodiments, the adapter sequences are attached to the template nucleic acid molecule with an enzyme. The enzyme may be a ligase or a polymerase. The ligase may be any enzyme capable of ligating an oligonucleotide (RNA or DNA) to the template nucleic acid molecule. Suitable ligases include T4 DNA ligase and T4 RNA ligase, available commercially from New England Biolabs (Ipswich, Mass.). Methods for using ligases are well known in the art. The polymerase may be any enzyme capable of adding nucleotides to the 3' and the 5' terminus of template nucleic acid molecules.

The ligation may be blunt ended or via use of complementary overhanging ends. In certain embodiments, following fragmentation, the ends of the fragments may be repaired, trimmed (e.g. using an exonuclease), or filled (e.g., using a polymerase and dNTPs) to form blunt ends. In some embodiments, end repair is performed to generate blunt end 5' phosphorylated nucleic acid ends using commercial kits, such as those available from Epicentre Biotechnologies (Madison, Wis.). Upon generating blunt ends, the ends may be treated with a polymerase and dATP to form a template independent addition to the 3'-end and the 5'-end of the fragments, thus producing a single A overhanging. This single A is used to guide ligation of fragments with a single T overhanging from the 5'-end in a method referred to as T-A cloning.

Alternatively, because the possible combination of overhangs left by the restriction enzymes are known after a restriction digestion, the ends may be left as-is, i.e., ragged ends. In certain embodiments double stranded oligonucleotides with complementary overhanging ends are used.

In certain embodiments, a single bar code is attached to each fragment. In other embodiments, a plurality of bar codes, e.g., two bar codes, are attached to each fragment.

A bar code sequence generally includes certain features that make the sequence useful in sequencing reactions. For example the bar code sequences are designed to have minimal or no homopolymer regions, i.e., 2 or more of the same base in a row such as AA or CCC, within the bar code sequence. The bar code sequences are also designed so that they are at least one edit distance away from the base addition order when performing base-by-base sequencing, ensuring that the first and last base do not match the expected bases of the sequence.

The bar code sequences are designed such that each sequence is correlated to a particular portion of nucleic acid, allowing sequence reads to be correlated back to the portion from which they came. Methods of designing sets of bar code sequences is shown for example in U.S. Pat. No. 6,235,475, the contents of which are incorporated by reference herein in their entirety. In certain embodiments, the bar code sequences range from about 5 nucleotides to about 15 nucleotides. In a particular embodiment, the bar code sequences range from about 4 nucleotides to about 7 nucleotides. Since the bar code sequence is sequenced along with the template nucleic acid, the oligonucleotide length should be of minimal length so as to permit the longest read from the template nucleic acid attached. Generally, the bar code sequences are spaced from the template nucleic acid molecule by at least one base (minimizes homopolymeric combinations).

Methods of the invention involve attaching the bar code sequences to the template nucleic acids. In certain embodiments, the bar code sequences are attached to the template nucleic acid molecule with an enzyme. The enzyme may be a ligase or a polymerase, as discussed above. Attaching bar code sequences to nucleic acid templates is shown in U.S. Pub. 2008/0081330 and U.S. Pub. 2011/0301042, the content of each of which is incorporated by reference herein in its entirety. Methods for designing sets of bar code sequences and other methods for attaching bar code sequences are shown in U.S. Pat. Nos. 6,138,077; 6,352,828; 5,636,400; 6,172,214; 6235,475; 7,393,665; 7,544,473; 5,846,719; 5,695,934; 5,604,097; 6,150,516; RE39,793; 7,537,897; 6,172,218; and 5,863,722, the content of each of which is incorporated by reference herein in its entirety.

After any processing steps (e.g., obtaining, isolating, fragmenting, or amplification), nucleic acid can be sequenced according to certain embodiments of the invention.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used in the methods of the provided invention includes, for example, 454 sequencing (454 Life Sciences, a Roche company, Branford, Conn.) (Margulies, M et al., Nature, 437:376-380 (2005); U.S. Pat. No. 5,583,024; U.S. Pat. No. 5,674,713; and U.S. Pat. No. 5,700,673). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology by Applied Biosystems from Life Technologies Corporation (Carlsbad, Calif.). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing, described, for example, in U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and are attached at a resolution such that the fragments are individually resolvable. Addition of one or more nucleotides releases a proton ($H^+$), which signal is detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pub. 2011/0009278, U.S. Pub. 2007/

0114362, U.S. Pub. 2006/0024681, U.S. Pub. 2006/0292611, U.S. Pat. No. 7,960,120, U.S. Pat. No. 7,835,871, U.S. Pat. No. 7,232,656, U.S. Pat. No. 7,598,035, U.S. Pat. No. 6,306,597, U.S. Pat. No. 6,210,891, U.S. Pat. No. 6,828,100, U.S. Pat. No. 6,833,246, and U.S. Pat. No. 6,911,345, each of which are herein incorporated by reference in their entirety.

Another example of a sequencing technology that can be used in the methods of the provided invention includes the single molecule, real-time (SMRT) technology of Pacific Biosciences (Menlo Park, Calif.). In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni, G. V., and Meller, A., Clin Chem 53: 1996-2001 (2007)). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in U.S. Pub. 2009/0026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using a electron microscope (Moudrianakis E. N. and Beer M., PNAS, 53:564-71(1965)). In one example of the technique, individual DNA molecules are labeled using metallic labels that are distinguishable using an electron microscope. These molecules are then stretched on a flat surface and imaged using an electron microscope to measure sequences.

Sequencing according to embodiments of the invention generates a plurality of reads. Reads according to the invention generally include sequences of nucleotide data less than about 150 bases in length, or less than about 90 bases in length. In certain embodiments, reads are between about 80 and about 90 bases, e.g., about 85 bases in length. In some embodiments, methods of the invention are applied to very short reads, i.e., less than about 50 or about 30 bases in length. After obtaining sequence reads, they are further processed as diagrammed in FIG. 1.

Figure 1:
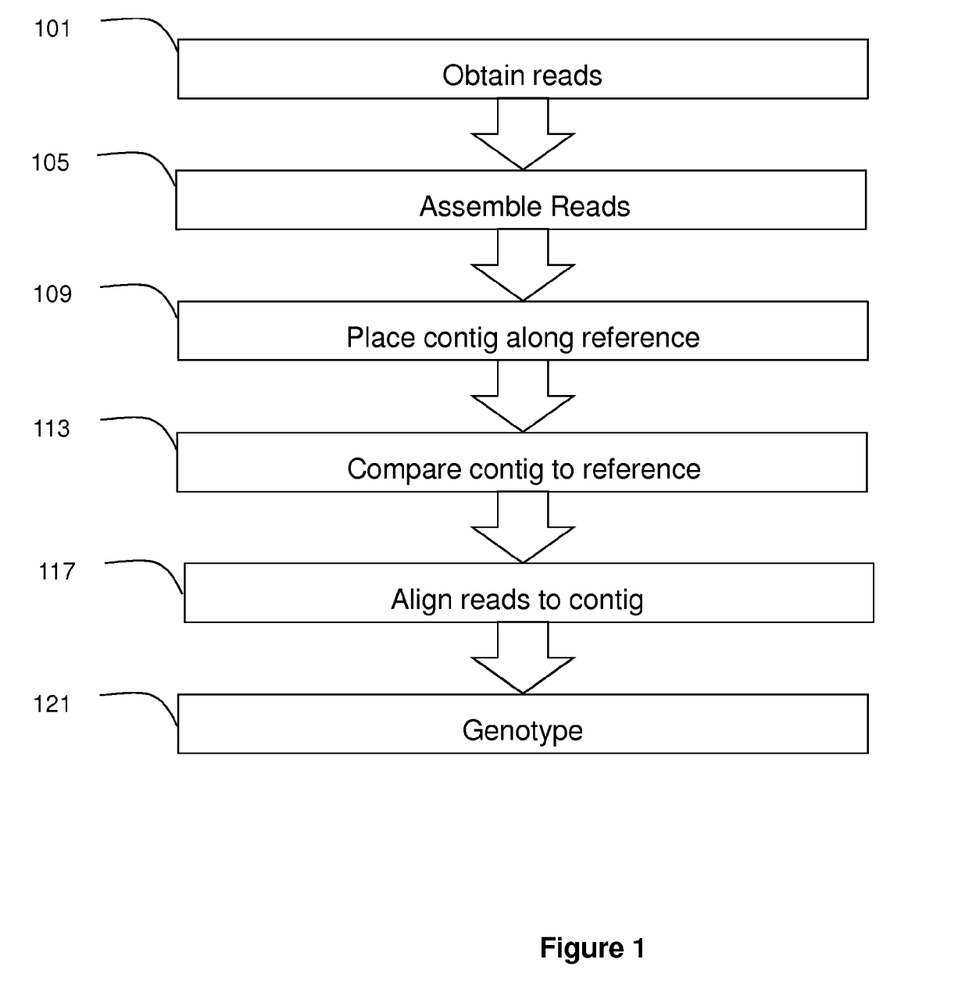
FIG. 1 is a diagram of methods of the invention.

FIG. 1 is a diagram of methods of the invention. Methods include obtaining 101 sequence reads and assembling 105 them into a contig, which is then aligned 109 to a reference. Differences are identified by comparison 113. The raw reads are aligned 117 to the contigs and positional and variant information is mapped to the reads from the reference via the contig, allowing genotyping 121 to be performed.

Figure 2:
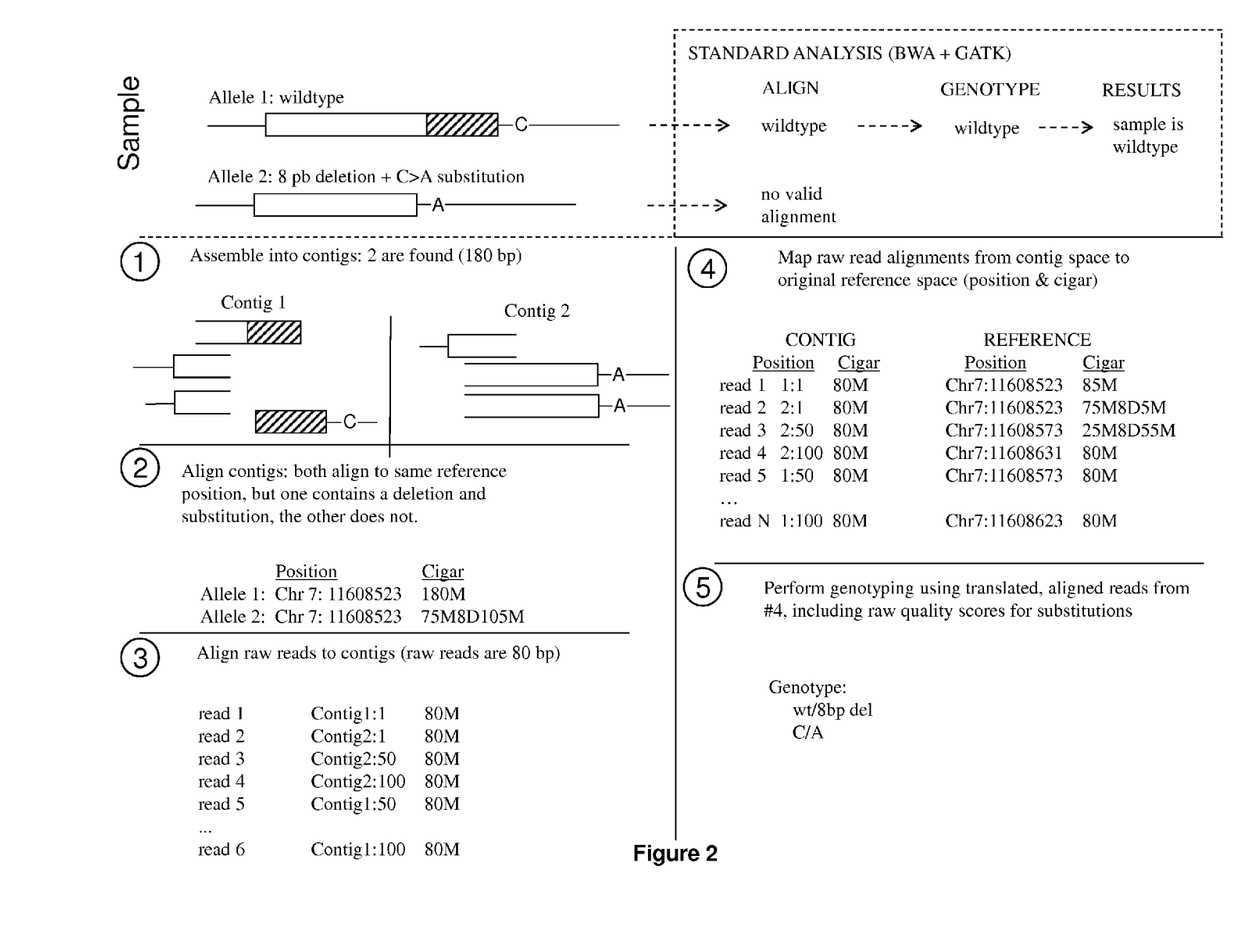
FIG. 2 illustrates an exemplary embodiment according to the invention.

FIG. 2 illustrates an exemplary embodiment according to methods of the invention. In step 1, reads are assembled into contigs. In the case of a single, homozygous target nucleic acid, a single contig per location is typically produced. Assembly can include any method including those discussed herein.

In step 2 shown in FIG. 2, each contig is aligned to a reference genome. Alignment can be by any method such as those discussed below, including, e.g., the bwa-sw algorithm implemented by BWA. As shown in FIG. 2, both align to the same reference position. Differences between the contig and the reference genome are identified and, as shown in FIG. 2, described by a CIGAR string.

In step 3, raw reads are aligned to contigs (using any method such as, for example, BWA with bwa-short and writing, for example, a CIGAR string).

As shown in FIG. 2, step 4, raw read alignments are mapped from contig space to original reference space (e.g., via position and CIGAR information).

In step 5, genotyping is performed using the translated, aligned reads from step 4 (e.g., including raw quality scores for substitutions).

A contig, generally, refers to the relationship between or among a plurality of segments of nucleic acid sequences, e.g., reads. Where sequence reads overlap, a contig can be represented as a layered image of overlapping reads. A contig is not defined by, nor limited to, any particular visual arrangement nor any particular arrangement within, for example, a text file or a database. A contig generally includes sequence data from a number of reads organized to correspond to a portion of a sequenced nucleic acid. A contig can include assembly results—such as a set of reads or information about their positions relative to each other or to a reference—displayed or stored. A contig can be structured as a grid, in which rows are individual sequence reads and columns include the base of each read that is presumed to align to that site. A consensus sequence can be made by identifying the predominant base in each column of the assembly. A contig according to the invention can include the visual display of reads showing them overlap (or not, e.g., simply abutting) one another. A contig can include a set of coordinates associated with a plurality of reads and giving the position of the reads relative to each other. A contig can include data obtained by transforming the sequence data of reads. For example, a Burrows-Wheeler transformation can be performed on the reads, and a contig can include the transformed data without necessarily including the untransformed sequences of the reads. A Burrows-Wheeler transform of nucleotide sequence data is described in U.S. Pub. 2005/0032095, herein incorporated by reference in its entirety.

Reads can be assembled into contigs by any method known in the art. Algorithms for the de novo assembly of a plurality of sequence reads are known in the art. One algorithm for assembling sequence reads is known as overlap consensus assembly. Overlap consensus assembly uses the overlap between sequence reads to create a link between them. The reads are generally linked by regions that overlap enough that non-random overlap is assumed Linking together reads in this way produces a contig or an overlap graph in which each node corresponds to a read and an edge represents an overlap between two reads. Assembly with overlap graphs is described, for example, in U.S. Pat. No. 6,714,874.

In some embodiments, de novo assembly proceeds according to so-called greedy algorithms. For assembly according to greedy algorithms, one of the reads of a group of reads is selected, and it is paired with another read with which it exhibits a substantial amount of overlap—generally it is paired with the read with which it exhibits the most overlap of all of the other reads. Those two reads are merged to form a new read sequence, which is then put back in the group of reads and the process is repeated. Assembly according to a greedy algorithm is described, for example, in Schatz, et al., Genome Res., 20:1165-1173 (2010) and U.S. Pub. 2011/0257889, each of which is hereby incorporated by reference in its entirety.

In other embodiments, assembly proceeds by pairwise alignment, for example, exhaustive or heuristic (e.g., not exhaustive) pairwise alignment. Alignment, generally, is discussed in more detail below. Exhaustive pairwise alignment, sometimes called a "brute force" approach, calculates an alignment score for every possible alignment between every possible pair of sequences among a set. Assembly by heuristic multiple sequence alignment ignores certain mathematically unlikely combinations and can be computationally faster. One heuristic method of assembly by multiple sequence alignment is the so-called "divide-and-conquer" heuristic, which is described, for example, in U.S. Pub. 2003/0224384. Another heuristic method of assembly by multiple sequence alignment is progressive alignment, as implemented by the program ClustalW (see, e.g., Thompson, et al., Nucl. Acids. Res., 22:4673-80 (1994)). Assembly by multiple sequence alignment in general is discussed in Lecompte, O., et al., Gene 270:17-30 (2001); Mullan, L. J., Brief Bioinform., 3:303-5 (2002); Nicholas, H. B. Jr., et al., Biotechniques 32:572-91(2002); and Xiong, G., Essential Bioinformatics, 2006, Cambridge University Press, New York, N.Y.

Assembly by alignment can proceed by aligning reads to each other or by aligning reads to a reference. For example, by aligning each read, in turn, to a reference genome, all of the reads are positioned in relationship to each other to create the assembly.

One method of assembling reads into contigs involves making a de Bruijn graph. De Bruijn graphs reduce the computation effort by breaking reads into smaller sequences of DNA, called k-mers, where the parameter k denotes the length in bases of these sequences. In a de Bruijn graph, all reads are broken into k-mers (all subsequences of length k within the reads) and a path between the k-mers is calculated. In assembly according to this method, the reads are represented as a path through the k-mers. The de Bruijn graph captures overlaps of length k−1 between these k-mers and not between the actual reads. Thus, for example, the sequencing CATGGA could be represented as a path through the following 2-mers: CA, AT, TG, GG, and GA. The de Bruijn graph approach handles redundancy well and makes the computation of complex paths tractable. By reducing the entire data set down to k-mer overlaps, the de Bruijn graph reduces the high redundancy in short-read data sets. The maximum efficient k-mer size for a particular assembly is determined by the read length as well as the error rate. The value of the parameter k has significant influence on the quality of the assembly. Estimates of good values can be made before the assembly, or the optimal value can be found by testing a small range of values. Assembly of reads using de Bruijn graphs is described in U.S. Pub. 2011/0004413, U.S. Pub. 2011/0015863, and U.S. Pub. 2010/0063742, each of which are herein incorporated by reference in their entirety.

Other methods of assembling reads into contigs according to the invention are possible. For example, the reads may contain barcode information inserted into template nucleic acid during sequencing. In certain embodiments, reads are assembled into contigs by reference to the barcode information. For example, the barcodes can be identified and the reads can be assembled by positioning the barcodes together.

In certain embodiments, assembly proceeds by making reference to supplied information about the expected position of the various reads relative to each other. This can be obtained, for example, if the subject nucleic acid being sequenced has been captured by molecular inversion probes, because the start of each read derives from a genomic position that is known and specified by the probe set design. Each read can be collected according to the probe from which it was designed and positioned according to its known relative offset. In some embodiments, information about the expected position of reads relative to each other is supplied by knowledge of the positions (e.g., within a gene) of an area of nucleic acid amplified by primers. For example, sequencing can be done on amplification product after a number of regions of the target nucleic acid are amplified using primer pairs designed or known to cover those regions. Reads can then be positioned during assembly at least based on which primer pair was used in an amplification that lead to those reads. Assembly of reads into contigs can proceed by any combination or hybrid of methods including, but not limited to, the above-referenced methods.

Assembly of reads into contigs is further discussed in Husemann, P. and Stoye, J, Phylogenetic Comparative Assembly, 2009, Algorithms in Bioinformatics: 9th International Workshop, pp. 145-156, Salzberg, S., and Warnow, T., Eds. Springer-Verlag, Berlin Heidelberg. Some exemplary methods for assembling reads into contigs are described, for example, in U.S. Pat. No. 6,223,128, U.S. Pub. 2009/0298064, U.S. Pub. 2010/0069263, and U.S. Pub. 2011/0257889, each of which is incorporated by reference herein in its entirety.

Computer programs for assembling reads are known in the art. Such assembly programs can run on a single general-purpose computer, on a cluster or network of computers, or on a specialized computing devices dedicated to sequence analysis.

Assembly can be implemented, for example, by the program 'The Short Sequence Assembly by k-mer search and 3' read Extension' (SSAKE), from Canada's Michael Smith Genome Sciences Centre (Vancouver, B.C., CA) (see, e.g., Warren, R., et al., Bioinformatics, 23:500-501 (2007)). SSAKE cycles through a table of reads and searches a prefix tree for the longest possible overlap between any two sequences. SSAKE clusters reads into contigs.

Another read assembly program is Forge Genome Assembler, written by Darren Platt and Dirk Evers and available through the SourceForge web site maintained by Geeknet (Fairfax, Va.) (see, e.g., DiGuistini, S., et al., Genome Biology, 10:R94 (2009)). Forge distributes its computational and memory consumption to multiple nodes, if available, and has therefore the potential to assemble large sets of reads. Forge was written in C++ using the parallel MPI library. Forge can handle mixtures of reads, e.g., Sanger, 454, and Illumina reads.

Assembly through multiple sequence alignment can be performed, for example, by the program Clustal Omega, (Sievers F., et al., Mol Syst Biol 7 (2011)), ClustalW, or ClustalX (Larkin M. A., et al., Bioinformatics, 23, 2947-2948 (2007)) available from University College Dublin (Dublin, Ireland).

Another exemplary read assembly program known in the art is Velvet, available through the web site of the European Bioinformatics Institute (Hinxton, UK) (Zerbino D. R. et al., Genome Research 18(5):821-829 (2008)). Velvet implements an approach based on de Bruijn graphs, uses information from read pairs, and implements various error correction steps.

Read assembly can be performed with the programs from the package SOAP, available through the website of Beijing Genomics Institute (Beijing, CN) or BGI Americas Corporation (Cambridge, Mass.). For example, the SOAPdenovo program implements a de Bruijn graph approach. SOAP3/GPU aligns short reads to a reference sequence.

Another read assembly program is ABySS, from Canada's Michael Smith Genome Sciences Centre (Vancouver, B.C., CA) (Simpson, J. T., et al., Genome Res., 19(6):1117-23 (2009)). ABySS uses the de Bruijn graph approach and runs in a parallel environment.

Read assembly can also be done by Roche's GS De Novo Assembler, known as gsAssembler or Newbler (NEW assemBLER), which is designed to assemble reads from the Roche 454 sequencer (described, e.g., in Kumar, S. et al., Genomics 11:571(2010) and Margulies, et al., Nature 437:376-380 (2005)). Newbler accepts 454 Flx Standard reads and 454 Titanium reads as well as single and paired-end reads and optionally Sanger reads. Newbler is run on Linux, in either 32 bit or 64 bit versions. Newbler can be accessed via a command-line or a Java-based GUI interface.

Cortex, created by Mario Caccamo and Zamin Iqbal at the University of Oxford, is a software framework for genome analysis, including read assembly. Cortex includes cortex_con for consensus genome assembly, used as described in Spanu, P. D., et al., Science 330(6010):1543-46 (2010). Cortex includes cortex_var for variation and population assembly, described in Iqbal, et al., De novo assembly and genotyping of variants using colored de Bruijn graphs, Nature Genetics (in press), and used as described in Mills, R. E., et al., Nature 470:59-65 (2010). Cortex is available through the creators' web site and from the SourceForge web site maintained by Geeknet (Fairfax, Va.).

Other read assembly programs include RTG Investigator from Real Time Genomics, Inc. (San Francisco, Calif.); iAssembler (Zheng, et al., BMC Bioinformatics 12:453 (2011)); TgiCL Assembler (Pertea, et al., Bioinformatics 19(5):651-52 (2003)); Maq (Mapping and Assembly with Qualities) by Heng Li, available for download through the SourceForge website maintained by Geeknet (Fairfax, Va.); MIRA3 (Mimicking Intelligent Read Assembly), described in Chevreux, B., et al., Genome Sequence Assembly Using Trace Signals and Additional Sequence Information, 1999, Computer Science and Biology: Proceedings of the German Conference on Bioinformatics (GCB) 99:45-56; PGA4genomics (described in Zhao F., et al., Genomics. 94(4):284-6 (2009)); and Phrap (described, e.g., in de la Bastide, M. and McCombie, W. R., Current Protocols in Bioinformatics, 17:11.4.1-11.4.15 (2007)). CLC cell is a de Bruijn graph-based computer program for read mapping and de novo assembly of NGS reads available from CLC bio Germany (Muehltal, Germany).

Assembly of reads produces one or more contigs. In the case of a homozygous or single target sequencing, a single contig will be produced. In the case of a heterozygous diploid target, a rare somatic mutation, or a mixed sample, for example, two or more contigs can be produced. Each contig includes information from the reads that make up that contig.

Assembling the reads into contigs is conducive to producing a consensus sequence corresponding to each contig. In certain embodiments, a consensus sequence refers to the most common, or predominant, nucleotide at each position from among the assembled reads. A consensus sequence can represent an interpretation of the sequence of the nucleic acid represented by that contig.

The invention provides methods for positioning a consensus sequence or a contig along a reference genome. In certain embodiments, a consensus sequence or a contig is positioned on a reference through information from known molecular markers or probes. In some embodiments, protein-coding sequence data in a contig, consensus sequence, or reference genome is represented by amino acid sequence and a contig is positioned along a reference genome. In some embodiments, a consensus sequence or a contig is positioned by an alignment of the contig to a reference genome.

Alignment, as used herein, generally involves placing one sequence along another sequence, iteratively introducing gaps along each sequence, scoring how well the two sequences match, and preferably repeating for various position along the reference. The best-scoring match is deemed to be the alignment and represents an inference about the historical relationship between the sequences. In an alignment, a base in the read alongside a non-matching base in the reference indicates that a substitution mutation has occurred at that point. Similarly, where one sequence includes a gap alongside a base in the other sequence, an insertion or deletion mutation (an "indel") is inferred to have occurred. When it is desired to specify that one sequence is being aligned to one other, the alignment is sometimes called a pairwise alignment. Multiple sequence alignment generally refers to the alignment of two or more sequences, including, for example, by a series of pairwise alignments.

In some embodiments, scoring an alignment involves setting values for the probabilities of substitutions and indels. When individual bases are aligned, a match or mismatch contributes to the alignment score by a substitution probability, which could be, for example, 1 for a match and 0.33 for a mismatch. An indel deducts from an alignment score by a gap penalty, which could be, for example, −1. Gap penalties and substitution probabilities can be based on empirical knowledge or a priori assumptions about how sequences mutate. Their values affects the resulting alignment. Particularly, the relationship between the gap penalties and substitution probabilities influences whether substitutions or indels will be favored in the resulting alignment.

Stated formally, an alignment represents an inferred relationship between two sequences, x and y. For example, in some embodiments, an alignment A of sequences x and y maps x and y respectively to another two strings x' and y' that may contain spaces such that: (i) $|x'|=|y'|$; (ii) removing spaces from x' and y' should get back x and y, respectively; and (iii) for any i, x'[i] and y'[i] cannot be both spaces.

A gap is a maximal substring of contiguous spaces in either x' or y'. An alignment A can include the following three kinds of regions: (i) matched pair (e.g., x'[i]=y'[i]); (ii) mismatched pair, (e.g., x'[i]≠y'[i] and both are not spaces); or (iii) gap (e.g., either x'[i . . . j] or y'[i . . . j] is a gap). In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

In some embodiments, any pair has a score a defined by a 4×4 matrix B of substitution probabilities. For example, B(i, i)=1 and $0<B(i,j)_{i<>j}<1$ is one possible scoring system. For instance, where a transition is thought to be more biologically probable than a transversion, matrix B could include B(C,T) =0.7 and B(A,T)=0.3, or any other set of values desired or determined by methods known in the art.

Alignment according to some embodiments of the invention includes pairwise alignment. A pairwise alignment, generally, involves—for sequence Q (query) having m characters and a reference genome T (target) of n characters—finding and evaluating possible local alignments between Q and T. For any $1 \leq i \leq n$ and $1 \leq j \leq m$, the largest possible alignment score of T[h . . . i] and Q[k . . . j], where $h \leq i$ and $k \leq j$, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. In some embodiments an exhaustive pairwise alignment is performed, which generally includes a pairwise alignment as described above, in which all possible local alignments (optionally subject to some limiting criteria) between Q and T are scored.

In some embodiments, pairwise alignment proceeds according to dot-matrix methods, dynamic programming methods, or word methods. Dynamic programming methods generally implement the Smith-Waterman (SW) algorithm or the Needleman-Wunsch (NW) algorithm. Alignment according to the NW algorithm generally scores aligned characters according to a similarity matrix S(a,b) (e.g., such as the aforementioned matrix B) with a linear gap penalty d. Matrix S(a,b) generally supplies substitution probabilities. The SW algorithm is similar to the NW algorithm, but any negative scoring matrix cells are set to zero. The SW and NW algorithms, and implementations thereof, are described in more detail in U.S. Pat. No. 5,701,256 and U.S. Pub. 2009/0119313, both herein incorporated by reference in their entirety. Computer programs known in the art for implementing these methods are described in more detail below.

In certain embodiments, an exhaustive pairwise alignment is avoided by positioning a consensus sequence or a contig along a reference genome through the use of a transformation of the sequence data. One useful category of transformation according to some embodiments of the invention involve making compressed indexes of sequences (see, e.g., Lam, et al., Compressed indexing and local alignment of DNA, 2008, Bioinformatics 24(6):791-97). Exemplary compressed indexes include the FN-index, the compressed suffix array, and the Burrows-Wheeler Transform (BWT, described in more detail below).

In certain embodiments, the invention provides methods of alignment which avoid an exhaustive pairwise alignment by making a suffix tree (sometime known as a suffix trie). Given a reference genome T, a suffix tree for T is a tree comprising all suffices of T such that each edge is uniquely labeled with a character, and the concatenation of the edge labels on a path from the root to a leaf corresponds to a unique suffix of T. Each leaf stores the starting location of the corresponding suffix.

On a suffix tree, distinct substrings of T are represented by different paths from the root of the suffix tree. Then, Q is aligned against each path from the root up to cm characters (e.g., using dynamic programming). The common prefix structure of the paths also gives a way to share the common parts of the dynamic programming on different paths. A pre-order traversal of the suffix tree is performed; at each node, a dynamic programming table (DP table) is maintained for aligning the pattern and the path up to the node. More rows are added to the table while proceeding down the tree, and corresponding rows are deleted while ascending the tree.

In certain embodiments, a BWT is used to index reference T, and the index is used to emulate a suffix tree. The Burrows-Wheeler transform (BWT) (Burrow and Wheeler, 1994, A block-sorting lossless data compression algorithm, Technical Report 124, Digital Equipment Corporation, CA) was invented as a compression technique and later extended to support pattern matching. To perform a BWT, first let T be a string of length n over an alphabet E. Assume that the last character of T is a unique special character $, which is smaller than any character in E. The suffix array SA[0, n−1] of T is an array of indexes such that SA[i] stores the starting position of the i-th-lexicographically smallest suffix. The BWT of T is a permutation of T such that BWT [i]=T [SA[i]−1]. For example, if T='acaacg$', then SA=(8, 3, 1, 4, 2, 5, 6, 7), and BWT='gc$aaacc'.

Alignment generally involves finding the best alignment score among substrings of T and Q. Using a BWT of T speeds up this step by avoiding aligning substrings of T that are identical. This method exploits the common prefix structure of a tree to avoid aligning identical substrings more than once. Use of a pre-order traversal of the suffix tree generates all distinct substrings of T. Further, only substrings of T of length at most cm, where c is usually a constant bounded by 2, are considered, because the score of a match is usually smaller than the penalty due to a mismatch/insert/delete, and a substring of T with more than 2m characters has at most m matches and an alignment score less than 0. Implementation of the method for aligning sequence data is described in more detail in Lam, et al., Bioinformatics 24(6):791-97 (2008).

An alignment according to the invention can be performed using any suitable computer program known in the art.

One exemplary alignment program, which implements a BWT approach, is Burrows-Wheeler Aligner (BWA) available from the SourceForge web site maintained by Geeknet (Fairfax, Va.). BWA can align reads, contigs, or consensus sequences to a reference. BWT occupies 2 bits of memory per nucleotide, making it possible to index nucleotide sequences as long as 4G base pairs with a typical desktop or laptop computer. The pre-processing includes the construction of BWT (i.e., indexing the reference) and the supporting auxiliary data structures.

BWA implements two different algorithms, both based on BWT. Alignment by BWA can proceed using the algorithm bwa-short, designed for short queries up to ~200 bp with low error rate (<3%) (Li H. and Durbin R. Bioinformatics, 25:1754-60 (2009)). The second algorithm, BWA-SW, is designed for long reads with more errors (Li H. and Durbin R. (2010) Fast and accurate long-read alignment with Burrows-Wheeler Transform. Bioinformatics, Epub.). The BWA-SW component performs heuristic Smith-Waterman-like alignment to find high-scoring local hits. One skilled in the art will recognize that bwa-sw is sometimes referred to as "bwa-long", "bwa long algorithm", or similar. Such usage generally refers to BWA-SW.

An alignment program that implements a version of the Smith-Waterman algorithm is MUMmer, available from the SourceForge web site maintained by Geeknet (Fairfax, Va.). MUMmer is a system for rapidly aligning entire genomes, whether in complete or draft form (Kurtz, S., et al., Genome Biology, 5:R12 (2004); Delcher, A. L., et al., Nucl. Acids Res., 27:11 (1999)). For example, MUMmer 3.0 can find all 20-basepair or longer exact matches between a pair of 5-megabase genomes in 13.7 seconds, using 78 MB of memory, on a 2.4 GHz Linux desktop computer. MUMmer can also align incomplete genomes; it can easily handle the 100s or 1000s of contigs from a shotgun sequencing project, and will align them to another set of contigs or a genome using the NUCmer program included with the system. If the species are too divergent for a DNA sequence alignment to detect similarity, then the PROmer program can generate alignments based upon the six-frame translations of both input sequences.

Another exemplary alignment program according to embodiments of the invention is BLAT from Kent Informatics (Santa Cruz, Calif.) (Kent, W. J., Genome Research 4: 656-664 (2002)). BLAT (which is not BLAST) keeps an index of the reference genome in memory such as RAM. The index includes of all non-overlapping k-mers (except optionally for those heavily involved in repeats), where k=11 by default. The genome itself is not kept in memory. The index is used to find areas of probable homology, which are then loaded into memory for a detailed alignment.

Another alignment program is SOAP2, from Beijing Genomics Institute (Beijing, CN) or BGI Americas Corporation (Cambridge, Mass.). SOAP2 implements a 2-way BWT (Li et al., Bioinformatics 25(15):1966-67 (2009); Li, et al., Bioinformatics 24(5):713-14 (2008)).

Another program for aligning sequences is Bowtie (Langmead, et al., Genome Biology, 10:R25 (2009)). Bowtie indexes reference genomes by making a BWT.

Other exemplary alignment programs include: Efficient Large-Scale Alignment of Nucleotide Databases (ELAND) or the ELANDv2 component of the Consensus Assessment of Sequence and Variation (CASAVA) software (Illumina, San Diego, Calif.); RTG Investigator from Real Time Genomics, Inc. (San Francisco, Calif.); Novoalign from Novocraft (Selangor, Malaysia); Exonerate, European Bioinformatics Institute (Hinxton, UK) (Slater, G., and Birney, E., BMC Bioinformatics 6:31(2005)), Clustal Omega, from University College Dublin (Dublin, Ireland) (Sievers F., et al., Mol Syst Biol 7, article 539 (2011)); ClustalW or ClustalX from University College Dublin (Dublin, Ireland) (Larkin M. A., et al., Bioinformatics, 23, 2947-2948 (2007)); and FASTA, European Bioinformatics Institute (Hinxton, UK) (Pearson W. R., et al., PNAS 85(8):2444-8 (1988); Lipman, D. J., Science 227(4693):1435-41 (1985)).

With each contig aligned to the reference genome, any differences between the contig and the reference genome can be identified by a comparison 113 (FIG. 2). For example, a computer alignment program can report any non-matching pair of aligned bases, e.g., in a visual display or as a character string. Since the entire contig is aligned to the reference genome, instead of individual short reads, an incorrect position is improbable. Thus, any indels introduced here typically will represent differences between the nucleic acid and the reference.

Parameters of the alignment are optimized to ensure correct placement of the contig on the overall reference genome, for example, where the bwa-sw algorithm is used. Each mutation identified here in a contig or consensus sequence can be described as it exists in the nucleic acid with reference to the reference genome. For convenience, this could be referred to as a contig:reference description of a mutation. Identifying a mutation according to methods of the invention can include identifying 1, 2, or any number of mutations as revealed, for example, by comparing a contig or consensus sequence to a reference genome.

In certain embodiments, a computer program creates a display, file, or variable containing a description of the mutation or descriptions of a number of mutations. In some embodiments, a contig:reference description of mutations will be written in a file, e.g., a CIGAR string in a BAM format file.

Besides aligning the contigs to a reference, methods of the invention include analyzing the individual reads. Individual reads are aligned 117 (FIG. 2) to the contigs, and positional and variant information is mapped from the reference to the individual reads through the contig.

An alignment according to this step can be performed by a computer program using any suitable algorithm such as one of those discussed above. In certain embodiments, a pair-wise alignment is performed between a read and a contig and optionally iterated until each read of interest has been aligned. In certain embodiments, the reads are aligned to a contig using bwa-short as implemented by BWA. In some embodiments, only certain reads are aligned—for example, those having certain scores or those that were excluded from further analysis prior to or during assembly.

Parameters of this alignment can be optimized to ensure very highly sensitive detection of mutations and combinations of mutations. For example, because the position relative to the reference genome is established with confidence, a gap penalty can be decreased relative to a substitution probability. In this alignment step by these parameters, long indels, indel-proximal substitutions, and indels near the ends of reads are detected with fidelity.

Each read represents a portion of the nucleic acid from the sample that can be described with reference to the contig. For convenience's sake, this could be referred to as a read:contig description. In certain embodiments, a computer program creates a display, file, or variable containing a read:contig description. The read:contig description can be written in a file, e.g., a CIGAR string in a BAM format file.

The output of the local alignment, describing the read with regards to the contig, can be combined with the output of the reference alignment, describing the contig with regards to the reference genome. Thus, the portion of nucleic acid represented by a read is determined to be related to a corresponding portion of the genome by the combination of alignments. This can be expressed, for example, by combining a read:contig description with a contig:reference description to produce a read:reference description. In this way, a target can be genotyped 121, as shown in FIG. 2.

This combination gives, for any mutation detected in the nucleic acid, a description of that mutation by reference to the reference genome. That is, the difference relative to the reference for the individual reads is determined using alignments between the read and the mapped contig plus alignments between the mapped contig and the reference genome.

In some embodiments, a heterogeneous sample includes some reads that vary from the contig. For example, a contig may map to reference genome according to a contig:reference alignment with a 1 bp substitution. A read may map to the contig with a 8 bp deletion according to a read:contig alignment. Methods of the invention give the correct annotation for the read, relative to the reference, as a description including a 8 bp deletion and a 1 bp substitution.

In some embodiments, any or all of the steps of the invention are automated. For example, a Perl script or shell script can be written to invoke any of the various programs discussed above (see, e.g., Tisdall, Mastering Perl for Bioinformatics, O'Reilly & Associates, Inc., Sebastopol, Calif. 2003; Michael, R., Mastering Unix Shell Scripting, Wiley Publishing, Inc., Indianapolis, Ind. 2003). Alternatively, methods of the invention may be embodied wholly or partially in one or more dedicated programs, for example, each optionally written in a compiled language such as C++ then compiled and distributed as a binary. Methods of the invention may be implemented wholly or in part as modules within, or by invoking functionality within, existing sequence analysis platforms. In certain embodiments, methods of the invention include a number of steps that are all invoked automatically responsive to a single starting queue (e.g., one or a combination of triggering events sourced from human activity, another computer program, or a machine). Thus, the invention provides methods in which any or the steps or any combination of the steps can occur automatically responsive to a queue. Automatically generally means without intervening human input, influence, or interaction (i.e., responsive only to original or pre-queue human activity). In certain embodiments, a contig is aligned to a reference, a read is aligned to a contig, the two alignments are combined, and a mutation is identified based on the combination of the alignments, partially or entirely automatically.

By combining alignments according to methods of the invention, the limitations of a tradeoff between substitution sensitivity and deletion sensitivity are overcome. The output includes an accurate and sensitive interpretation of the subject nucleic. The output can be provided in the format of a computer file. In certain embodiments, the output is a FASTA file, VCF file, text file, or an XML file containing sequence data such as a sequence of the nucleic acid aligned to a sequence of the reference genome. In other embodiments, the output contains coordinates or a string describing one or more mutations in the subject nucleic acid relative to the reference genome. Alignment strings known in the art include Simple UnGapped Alignment Report (SUGAR), Verbose Useful Labeled Gapped Alignment Report (VULGAR), and Compact Idiosyncratic Gapped Alignment Report (CIGAR) (Ning, Z., et al., Genome Research 11(10):1725-9 (2001)). These strings are implemented, for example, in the Exonerate sequence alignment software from the European Bioinformatics Institute (Hinxton, UK).

In some embodiments, the output is a sequence alignment—such as, for example, a sequence alignment map (SAM) or binary alignment map (BAM) file—comprising a CIGAR string (the SAM format is described, e.g., in Li, et al., The Sequence Alignment/Map format and SAMtools, Bioinformatics, 2009, 25(16):2078-9). In some embodiments, CIGAR displays or includes gapped alignments one-per-line. CIGAR is a compressed pairwise alignment format reported as a CIGAR string. A CIGAR string is useful for representing long (e.g. genomic) pairwise alignments. A CIGAR string is used in SAM format to represent alignments of reads to a reference genome sequence.

An CIGAR string follows an established motif. Each character is preceded by a number, giving the base counts of the event. Characters used can include M, I, D, N, and S (M=match; I=insertion; D=deletion; N=gap; S=substitution).

The cigar line defines the sequence of matches/mismatches and deletions (or gaps). For example, the cigar line 2MD3M2D2M will mean that the alignment contains 2 matches, 1 deletion (number 1 is omitted in order to save some space), 3 matches, 2 deletions and 2 matches.

To illustrate, if the original sequence is AACGCTT and the CIGAR string is 2MD3M2D2M, the aligned sequence will be AA-CGG-TT. As a further example, if an 80 bp read aligns to a contig such that the first 5' nucleotide of the read aligns to the 50th nucleotide from the 5' end of the contig with no indels or substitutions between the read and the contig, the alignment will yield "80M" as a CIGAR string.

By combining alignments according to the methods described herein, one or more mutations in the nucleic acid can be detected, identified, or described. Mutations detectable by methods of the invention include substitutions, single nucleotide polymorphisms, insertions, deletions, translocations, epigenetic mutations, and copy number repeats. Methods of the invention detect and describe more than one mutation including, for example, two or more mutations. Mutations can be detected that are near each other, for example less than 1,000 nucleotides apart along a strand of nucleic acid. In a preferred embodiment, methods of the invention can detect two mutations within 100 bases of each other, and even within 10 bases of each other.

Methods of the invention can detect two mutations of different types near each other including, for example, a substitution near an indel. Mutations near the ends of sequence reads can be detected including, for example, an indel at or near an end of a read.

By detecting mutations with great sensitivity, methods of the invention can reliably detect disease-associated mutations. Disease associated mutations include known mutations and novel ones. In certain embodiments, methods of the invention detect mutations known to be associated with Tay-Sachs disease, Canavan disease, cystic fibrosis, familial dysautonomia, Bloom syndrome, Fanconi anemia group C, Gaucher disease, mucolipidosis type IV, Niemann-Pick disease type A, spinal muscular atrophy (SMA), Sickle cell anemia, Thalassemia, or novel mutations.

Other embodiments are within the scope and spirit of the invention. For example, due to the nature of software, functions described above can be implemented using software, hardware, firmware, hardwiring, or combinations of any of these. Features implementing functions can also be physically located at various positions, including being distributed such that portions of functions are implemented at different physical locations.

Figure 3:
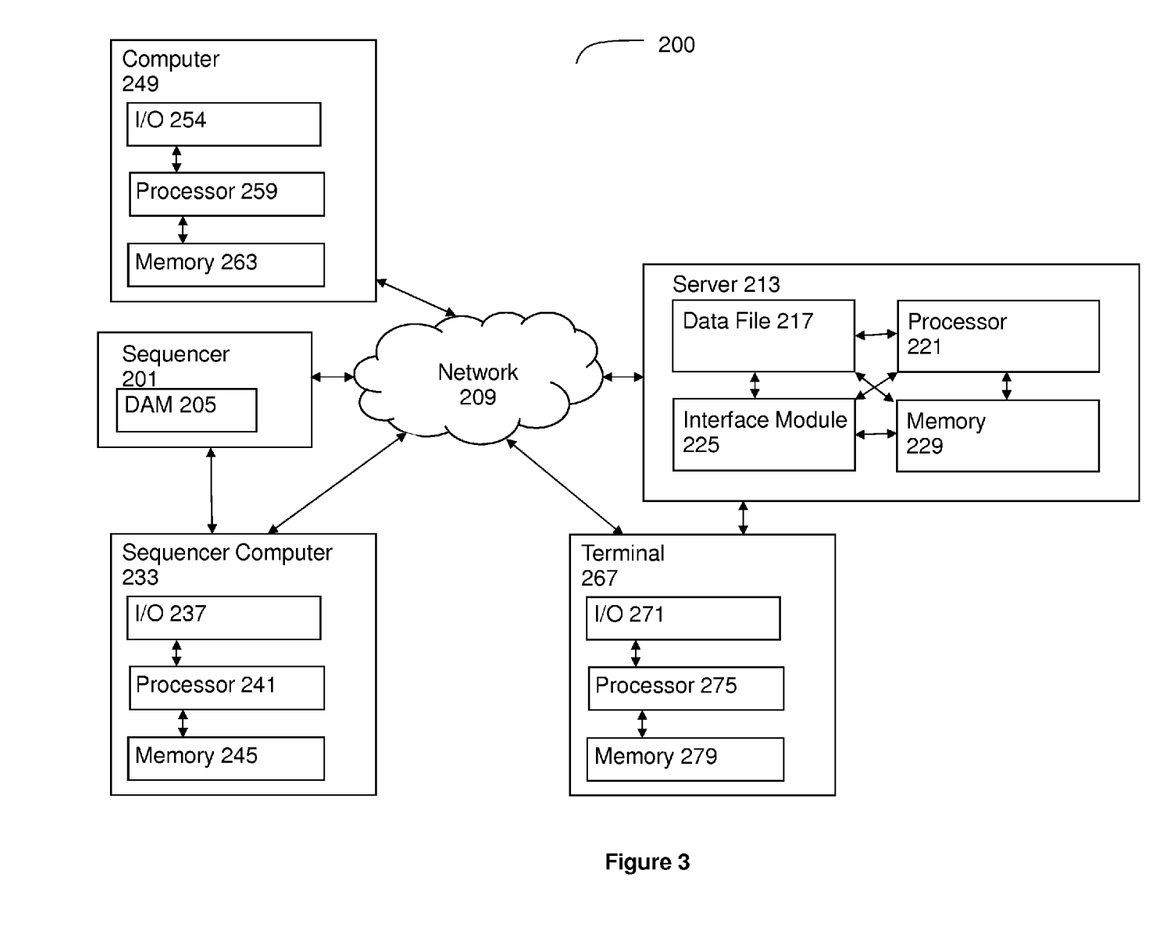
FIG. 3 illustrates a system for performing methods of the invention.

As one skilled in the art would recognize as necessary or best-suited for performance of the methods of the invention and sequence assembly in general, computer system 200 or machines of the invention include one or more processors (e.g., a central processing unit (CPU) a graphics processing unit (GPU) or both), a main memory and a static memory, which communicate with each other via a bus.

In an exemplary embodiment shown in FIG. 3, system 200 can include a sequencer 201 with data acquisition module 205 to obtain sequence read data. Sequencer 201 may optionally include or be operably coupled to its own, e.g., dedicated, sequencer computer 233 (including an input/output mechanism 237, one or more of processor 241 and memory 245). Additionally or alternatively, sequencer 201 may be operably coupled to a server 213 or computer 249 (e.g., laptop, desktop, or tablet) via network 209. Computer 249 includes one or more processor 259 and memory 263 as well as an input/output mechanism 254. Where methods of the invention employ a client/server architecture, an steps of methods of the invention may be performed using server 213, which includes one or more of processor 221 and memory 229, capable of obtaining data, instructions, etc., or providing results via interface module 225 or providing results as a file 217. Server 213 may be engaged over network 209 through computer 249 or terminal 267, or server 213 may be directly connected to terminal 267, including one or more processor 275 and memory 279, as well as input/output mechanism 271.

System 200 or machines according to the invention may further include, for any of I/O 249, 237, or 271 a video display unit (e.g., a liquid crystal display (LCD) or a cathode ray tube (CRT)). Computer systems or machines according to the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 263, 245, 279, or 229 according to the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media.

The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. The term "machine-readable medium" shall accordingly be taken to include, but not be limited to, solid-state memories (e.g., subscriber identity module (SIM) card, secure digital card (SD card), micro SD card, or solid-state drive (SSD)), optical and magnetic media, and any other tangible storage media.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Multiple (N) Reads from Two Alleles

A sample containing heterozygous human genomic nucleic acid is obtained.

A short human exon is captured by three different mutually overlapping molecular inversion probes. The sample is heterozygous. The nucleic acid is sequenced to produce N different reads, each 80 bp.

All reads derived from one of those probes (i.e., all reads beginning with the targeting sequence from one of the three probes) are collected and passed to the assembly algorithm together with their known relative offsets, which is known because the reads were sequenced from the probes.

This "subsetting" allows the efficiency of the assembly to be increased by seeding the assembly with information about the expected position of each given read relative to the others. Thus, the start of each read derives from a genomic position that is known and specified by the probe set design.

The reads are assembled into two contigs. Two contigs are found, each about 180 bp. Each contig contains a unique combination of indels and substitutions. One contig corresponds to allele 1 and the other contig corresponds to allele 2.

Each contig is aligned to a reference genome to determine the genomic position of each contig. Each contig aligns to substantially the same reference position.

For each contig, any difference between that contig and a reference genome is identified, where differences includes substitutions and indels. This is done using BWA-long, which returns a BAM format file containing the alignment of the contig and a CIGAR string describing any differences from the reference sequence. One contains a deletion and a substitution, relative to the reference. The position for the allele 1 contig (Contig1) is chromosome 7:11608523 and the CIGAR string for the allele 1 contig is 180M. The position for the allele 2 contig (Contig2) is chromosome 7:11608523 and the CIGAR string for the allele 1 contig is 75M8D105M.

The increased sequence context provided by the assembled reads (contigs) improves the overall mapping accuracy. For example, the probes are more likely to map uniquely to the reference genome as an assembled contig than as individual reads.

The local, contig-specific alignment of each raw read is determined using BWA-short, with appropriate adjustments to substitution and gap penalties to ensure accurate placement of each read to its respective contig. That is, each raw read is aligned to the contig with which it is associated. The positions and CIGAR strings are given in Table 1.

TABLE 1

Position and CIGAR string of each read

| Read | Position | CIGAR string |
|---|---|---|
| 1 | Contig1:1 | 80M |
| 2 | Contig2:1 | 80M |
| 3 | Contig2:50 | 80M |
| 4 | Contig2:100 | 80M |
| 5 | Contig1:50 | 80M |
| 6 | Contig1:100 | 80M |

For each raw read, any difference between that read and contig to which it has been aligned is identified (i.e., as represented by the entries in the CIGAR string column in Table 1). Most differences will represent sequencing errors (since most common variations will typically be captured in the contigs themselves). However, some differences between a raw read and a contig will be evidence of rare alleles if the sample being analyzed is, e.g., a hetergenous population of cells or ploidy other than diploid. The output of this alignment is in BAM format.

The alignments of the raw reads to the contigs are converted into global, reference-based alignments. Specifically, the coordinates are converted to reference coordinates (multiple contigs can map to the same reference position). For each individual read, the differences between that read and the reference are determined using the differences between that read and the mapped contig plus the differences between the mapped contig and the reference.

TABLE 2

Map of raw read alignments from contig space to original reference space

| Read | Position of Read in Contig | Read to Contig CIGAR string | Position of Contig in Reference | Read to Reference CIGAR string |
| --- | --- | --- | --- | --- |
| 1 | Contig1:1 | 80M | Chr7:11608523 | 85M |
| 2 | Contig2:1 | 80M | Chr7:11608523 | 75M8D5M |
| 3 | Contig2:50 | 80M | Chr7:11608573 | 25M8D55M |
| 4 | Contig2:100 | 80M | Chr7:11608631 | 80M |
| 5 | Contig1:50 | 80M | Chr7:11608573 | 80M |
| 6 | Contig2:50 | 30MS49M | Chr7:11608573 | 25M8D5MS49M |
| . | | | | |
| . | | | | |
| . | | | | |
| N | Contig1:100 | 80M | Chr7:11608623 | 80M |

One contig (Contig2) maps to the reference with an 8 bp deletion. One individual read (Read 6) maps to that contig with a 1 bp substitution only. The correct annotation for this read, relative to the reference, is 8 bp deletion and 1 bp substitution. The CIGAR string in the BAM file is adjusted accordingly. The adjusted CIGAR string for Read 6 is 25M8D5MS49M, indicating that, beginning at position 11,608,573 of chromosome 7, Read 6 matches chromosome 7 for 25 bases, then has an 8 base deletion followed by 5 matching bases, then 1 substitution, followed by 49 more matching bases. Thus, an indel and a substitution proximal to each other on the nucleic acid and captured in Read 6 are described as mutations relative to the wild-type reference genome.

The genotype is assessed (i.e., for substitutions or indels) on the output BAM file. This allows for the detection of large indels and allows for accurate, quality score-based genotyping of substitutions near indels.

Example 2

Assemblies of Subsets

A sample containing a nucleic acid containing three exons is obtained.

Each exon is defined by a set of probe arms that covers it. Each exon is captured by the probes and sequenced to produce a plurality of reads, each approximately 85 bp.

All reads are collected and passed to the assembly algorithm and are subset going into the assembly using the probe arms. Each subset includes those reads associated with one set of probe arms. This reduces the runtime of the assembly drastically, relative to assembly without subsetting the reads, because assembly time is exponential to number of reads.

Each subset is assembled into a contig. Since each subset corresponds to a set of probe arms, and each exon is defined as the set of probe arms that covers it, three contigs are found.

Each contig is aligned to a reference using BWA-long and any differences are found and recorded as a position and a CIGAR string in a contig:reference BAM format file. This alignment step captures and stores variant information about the sample and thus the reads. The variant information is transferred through to the individual reads by aligning them to the contigs to produce a read:contig BAM file and mapping the first alignment onto the second. The individual reads are thus translated to include the variant and positional information.

Each exon in the nucleic acid from the sample is then genotyped based on the translated reads.

What is claimed is:

1. A method for identifying a mutation in a nucleic acid, the method comprising:
    sequencing nucleic acid to generate a plurality of sequence reads;
    creating a contig based on the reads;
    aligning the contig to a reference sequence;
    aligning the individual reads back to the contig; and
    identifying a mutation based on the alignments to the contig and the reference sequence.

2. The method of claim 1, further comprising splitting the reads into subsets corresponding to known locations.

3. The method of claim 1, further comprising identifying a mutation in the contig relative to the reference.

4. The method of claim 1 further comprising determining a position of the mutation in the nucleic acid based on a position of the mutation in the reads and the alignments to the contig and the reference sequence.

5. The method of claim 1 wherein the mutation is selected from the group consisting of: a single nucleotide polymorphism (SNP), an insertion, a deletion, a substitution, a translocation, an epigenetic mutation, and a copy number repeat.

6. The method of claim 1 wherein a plurality of mutations are identified.

7. The method of claim 6 wherein a first mutation is within about 100 nucleotides of a second mutation.

8. The method according to claim 7, wherein the first mutation is a substitution and the second mutation is a deletion.

9. The method of claim 1 wherein the mutation is a deletion at an end of a sequence read.

10. The method of claim 1, wherein the mutation is associated with a disease.

11. The method according to claim 1, wherein sequencing is sequencing-by-synthesis.

12. The method according to claim 11, wherein sequencing-by-synthesis is single molecule sequencing-by-synthesis.

* * * * *